US010393591B2

(12) United States Patent
Yang et al.

(10) Patent No.: US 10,393,591 B2
(45) Date of Patent: Aug. 27, 2019

(54) ELECTROMAGNETIC RADIATION DETECTOR USING A PLANAR GOLAY CELL

(71) Applicant: Honeywell International Inc., Morris Plains, NJ (US)

(72) Inventors: Wei Yang, Minnetonka, MN (US); Teresa M. Marta, White Bear Lake, MN (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 15/767,100

(22) PCT Filed: Oct. 6, 2016

(86) PCT No.: PCT/US2016/055759
§ 371 (c)(1),
(2) Date: Apr. 9, 2018

(87) PCT Pub. No.: WO2017/062626
PCT Pub. Date: Apr. 13, 2017

(65) Prior Publication Data
US 2018/0299330 A1    Oct. 18, 2018

Related U.S. Application Data

(60) Provisional application No. 62/239,658, filed on Oct. 9, 2015.

(51) Int. Cl.
G01J 5/08    (2006.01)
G01J 5/42    (2006.01)
G01N 21/3518    (2014.01)

(52) U.S. Cl.
CPC .............. G01J 5/42 (2013.01); G01J 5/0853 (2013.01); G01N 21/3518 (2013.01); G01J 2005/425 (2013.01)

(58) Field of Classification Search
CPC .................................. G01J 5/0853; G01J 5/42
See application file for complete search history.

(56) References Cited

U.S. PATENT DOCUMENTS 2,424,976 A    8/1947    Golay et al.
2,924,713 A    2/1960    Liston
(Continued)

FOREIGN PATENT DOCUMENTS

AU    582290 B    3/1989
CN    108351293 A    7/2018
(Continued)

OTHER PUBLICATIONS

Schjolberg-Henriksen, et al.: "Sensitive and Selective Photo Acoustic Gas Sensor Suitable for High Volume Manifacturing", IEEE Sensors 2006, EXCO, Deagu Korea, Oct. 22-25, 2006, pp. 679-682.
(Continued)

Primary Examiner — Mark R Gaworecki
(74) Attorney, Agent, or Firm — Wick Phillips Gould & Martin, LLP

(57) ABSTRACT

Embodiments relate generally to electromagnetic radiation detector devices, systems, and methods using a planar Golay cell. One device includes a cell body forming a cavity therein, wherein the cavity includes a wavelength selective absorber having a predetermined absorption spectral range and the cavity is filled with a gas and a pressure sensing element fluidly connected to the cavity to measure a change in pressure within the cavity. One device may include a plurality of planar Golay cells, wherein the cell bodies of the Golay cells are stacked against one another, wherein the pressure sensing elements of the Golay cells are located adjacent to the stacked sides of the cell bodies, and wherein radiation from a single light source is directed through the plurality of Golay cells.

20 Claims, 3 Drawing Sheets

(56) References Cited

U.S. PATENT DOCUMENTS

| | | |
|---|---|---|
| 4,436,428 A | 3/1984 | Watanabe et al. |
| 4,492,862 A | 1/1985 | Grynberg et al. |
| 4,535,241 A | 8/1985 | Eberhardt |
| 4,557,603 A | 12/1985 | Oehler et al. |
| 4,692,622 A | 9/1987 | Taniguchi et al. |
| 4,736,103 A | 4/1988 | Nelson et al. |
| 4,738,266 A | 4/1988 | Thatcher |
| 4,740,086 A | 4/1988 | Oehler et al. |
| 4,891,629 A | 1/1990 | Gajjar et al. |
| 4,903,248 A | 2/1990 | Fertig |
| 5,055,690 A | 10/1991 | Bonne |
| 5,394,934 A | 5/1995 | Rein et al. |
| 5,468,961 A | 11/1995 | Gradon et al. |
| 5,498,873 A | 3/1996 | Liebermann et al. |
| 5,559,333 A | 9/1996 | Araya et al. |
| 5,616,826 A | 4/1997 | Pellaux |
| 5,886,249 A | 3/1999 | Bonne et al. |
| 5,892,140 A | 4/1999 | Wood |
| 6,067,840 A | 5/2000 | Chelvayohan et al. |
| 6,222,190 B1 | 4/2001 | Bernstein et al. |
| 6,327,896 B1 | 12/2001 | Veronesi et al. |
| 6,469,303 B1 | 10/2002 | Sun et al. |
| 6,552,792 B1 | 4/2003 | Pilgrim et al. |
| 6,628,396 B1 | 9/2003 | Gul |
| 6,853,449 B2 | 2/2005 | Hocker |
| 6,878,940 B2 | 4/2005 | Nakamura et al. |
| 7,034,943 B1 | 4/2006 | Moeckli et al. |
| 7,045,784 B1 | 5/2006 | Ptasinski et al. |
| 7,214,939 B1 | 5/2007 | Wong |
| 7,288,766 B2 | 10/2007 | Uchida et al. |
| 7,477,993 B2 | 1/2009 | Sunshine et al. |
| 7,663,756 B2 | 2/2010 | Cole |
| 7,738,116 B2 | 6/2010 | Kauppinen |
| 7,797,983 B2 | 9/2010 | Kauppinen |
| 7,808,640 B2 | 10/2010 | Fritz et al. |
| 7,895,880 B2 | 3/2011 | Fritz et al. |
| 7,958,771 B2 | 6/2011 | Rezachek |
| 7,961,313 B2 | 6/2011 | Van Neste et al. |
| 8,085,403 B2 | 12/2011 | Fritz et al. |
| 8,312,758 B2 | 11/2012 | Tobias |
| 8,322,191 B2 | 12/2012 | Fritz |
| 8,373,568 B2 | 2/2013 | Moe et al. |
| 8,451,447 B2 | 5/2013 | Fritz et al. |
| 8,584,508 B2 | 11/2013 | Rezachek |
| 8,594,507 B2 | 11/2013 | Youngner et al. |
| 8,661,874 B2 | 3/2014 | Rezachek |
| 8,689,607 B2 | 4/2014 | Rezachek et al. |
| 8,695,402 B2 | 4/2014 | Thorson |
| 8,701,465 B2 | 4/2014 | Shubinsky et al. |
| 8,746,038 B2 | 6/2014 | Rezachek |
| 8,806,916 B2 | 8/2014 | Gautieri |
| 8,848,191 B2 | 9/2014 | Lust |
| 8,939,006 B2 | 1/2015 | Rezachek et al. |
| 9,086,364 B2 | 7/2015 | Rezachek et al. |
| 9,243,998 B2 | 1/2016 | Avramescu et al. |
| 9,606,049 B1 | 3/2017 | Yang et al. |
| 9,829,428 B2 | 11/2017 | Yang et al. |
| 2004/0036023 A1 | 2/2004 | Hodgkinson |
| 2006/0138327 A1 | 6/2006 | Kauppinen |
| 2006/0175547 A1 | 8/2006 | DiFoggio et al. |
| 2008/0035848 A1 | 2/2008 | Wong |
| 2008/0277586 A1 | 11/2008 | Cardinale |
| 2011/0032514 A1 | 2/2011 | Bitter et al. |
| 2011/0296900 A1 | 12/2011 | Thorson |
| 2012/0055232 A1 | 3/2012 | Thornson |
| 2013/0008229 A1 | 1/2013 | Avramescu et al. |
| 2013/0086977 A1 | 4/2013 | Wong |
| 2014/0091014 A1 | 4/2014 | Wagner et al. |
| 2015/0101395 A1 | 4/2015 | Dehe et al. |
| 2017/0102318 A1 | 4/2017 | Yang et al. |
| 2017/0115207 A1 | 4/2017 | Yang et al. |
| 2018/0045563 A1 | 2/2018 | Marta et al. |
| 2018/0284012 A1 | 10/2018 | Marta et al. |
| 2018/0299369 A1 | 10/2018 | Marta et al. |

FOREIGN PATENT DOCUMENTS

| | | |
|---|---|---|
| CN | 108369139 A | 8/2018 |
| DE | 2926662 A1 | 1/1981 |
| DE | 3508027 A1 | 9/1986 |
| DE | 19841491 A1 | 11/2008 |
| DE | 102007020596 A1 | 11/2008 |
| DE | 102008018504 A1 | 10/2009 |
| DE | 102012217479 B3 | 10/2013 |
| EP | 1546683 | 8/2004 |
| EP | 2060891 A1 | 5/2009 |
| EP | 2148184 A2 | 1/2010 |
| EP | 2402735 A2 | 1/2012 |
| EP | 2148184 A3 | 12/2012 |
| EP | 3265766 A1 | 1/2018 |
| EP | 3347697 A1 | 7/2018 |
| EP | 3347698 A1 | 7/2018 |
| EP | 3359933 A1 | 8/2018 |
| EP | 3359934 A1 | 8/2018 |
| GB | 710867 | 6/1954 |
| GB | 2358245 A | 7/2001 |
| IN | 288304 | 10/2017 |
| JP | H05172627 A | 7/1993 |
| JP | H05172628 A | 7/1993 |
| JP | H05272628 A | 7/1993 |
| JP | 08184501 | 7/1996 |
| JP | 408184501 | 7/1996 |
| JP | H10332579 A | 12/1998 |
| JP | H1172428 A | 3/1999 |
| JP | 2002328116 A | 11/2002 |
| JP | 2007170841 A | 7/2007 |
| JP | 2009257808 A | 11/2009 |
| JP | 2010126465 A | 6/2010 |
| JP | 2010128781 A | 6/2010 |
| JP | 5028080 B2 | 9/2012 |
| SG | 158463 | 2/2010 |
| WO | 9624831 A1 | 8/1996 |
| WO | 9812522 A1 | 3/1998 |
| WO | 2008074442 A1 | 6/2008 |
| WO | 2016141155 A1 | 9/2016 |
| WO | 2017044435 A1 | 3/2017 |
| WO | 2017044436 A1 | 3/2017 |
| WO | 2017062617 A1 | 4/2017 |
| WO | 2017062626 A1 | 4/2017 |

OTHER PUBLICATIONS

PCT Application No. PCT/US2016/050455, International Search Report, dated Dec. 7, 2016, 5 pages.

PCT Application No. PCT/US2016/050455, Written Opinion of the International Searching Authority, dated Dec. 7, 2016, 7 pages.

Dundas M E: "New Technologies in Infrared Hydrocarbon Detection", ISA Transactions, Instrument Society of America, Pittsburgh, U.S., vol. 31, No. 4, 1992, pp. 51-65.

Anonymous: "Flammability limit—Wikipedia, the free encyclopedia", Oct. 21, 2014 (Oct. 21, 2014), Retrieved from the Internet: URL: http://web.archive.org/web/20141021101901/http://en.wikipedia.org/wiki/Flammability_limit [retrieved on Nov. 24, 2016] substance table with LEL values; p. 4-p. 8.

PCT Application No. PCT/US2016/050456, International Search Report, dated Dec. 12, 2016, 5 pages.

PCT Application No. PCT/US2016/050456, Written Opinion of the International Searching Authority, dated Dec. 12, 2016, 7 pages.

PCT Application No. PCT/US2016/055759, International Search Report, dated Jan. 23, 2017, 4 pages.

PCT Application No. PCT/US2016/055759, Written Opinion of the International Searching Authority, dated Jan. 23, 2017, 7 pages.

David Klocke et al: "Infrared receptors in pyrophilous ("fire loving") insects as model for new un-cooled infrared sensors". Beilstein Journal of Nanotechnology, vol. 2, Mar. 30, 2011, pp. 186-197.

PCT Application No. PCT/US2016/055748, International Search Report, dated Dec. 23, 2016, 4 pages.

PCT Application No. PCT/US2016/055748, Written Opinion of the International Searching Authority, dated Dec. 23, 2016, 7 pages.

(56) References Cited

OTHER PUBLICATIONS

Yamashita K et al.: "Miniaturized infrared sensor using silicon diaphragm based on Golay cell", Sensors and Actuators A:L Physical, Elsevier BV, NL, vol. 66, No. 1-3, Apr. 1, 1998, pp. 29-32.
Feiertag G et al.: "Flip Chip MEMS microphone package with large acoustic reference volume", Procedia Engineering, Elsevier, Amsterdam, NL, vol. 5, Jan. 1, 2010, pp. 355-358.
Kari Schjølberg-Henriksen et al.: "Sensitive and Selective Photo Acoustic Gas Sensor Suitable for High Volume Manufacturing", IEEE Sensors 2006, EXCO, Deagu Korea, Oct. 22-25, 2006, pp. 679-682.
U.S. Appl. No. 14/879,920, Notice of Allowance, dated Oct. 7, 2016, 15 pages.
U.S. Appl. No. 14/879,920, Corrected Notice of Allowability, dated Feb. 22, 2017, 6 pages.
U.S. Appl. No. 15/400,554, Office Action, dated Mar. 3, 2017, 16 pages.
U.S. Appl. No. 15/400,554, Notice of Allowance, dated Jul. 18, 2017, 16 pages.
Kari Schjølberg-Henriksen et al., "Sensitive and Selective Photo Acoustic Gas Sensor Suitable for High Volume Manufacturing", IEEE Sensors Journal, vol. 8, No. 9, Sep. 2008, pp. 1539-1545.
PCT Application No. PCT/US2016/050455, International Preliminary Report on Patentability, dated Mar. 22, 2018, 9 pages.
Europe Patent Application No. 16766771.6, 2018, Communication Pursuant to Rules 161(1) and 162 EPC, dated Apr. 18, 2018, 3 pages.
PCT Application No. PCT/US2016/050456, International Preliminary Report on Patentability, dated Mar. 13, 2018, 8 pages.
U.S. Appl. No. 15/759,158 entitled "Gas Detector With Normalized Response and Improved Sensitivity", filed Mar. 9, 2018, 49 pages.
Christopher Grinde et al., "A Clover Shaped Silicon Piezoresistive Microphone for Miniaturized Photoacoustic Gas Sensors," Symposium on Design, Test, Integration & Packaging of MEMS/MOEMS, 2009. DTIP MEMS/MOEMS 09, pp. 256-260. Retrieved from the Internet <URL: http://www.eda-publishing.org/dtip09_proceedings.pdf#page=270>.
International Application No. PCT/US2016/055748, International Preliminary Report on Patentability, dated Apr. 10, 2018, 8 pages.
Europe Patent Application No. 16785292.0, Communication pursuant to Rules 161(1) and 162 EPC, dated May 17, 2018, 3 pages.
International Application No. PCT/US2016/055759, International Preliminary Report on Patentability dated Apr. 10, 2018, 8 pages.
Europe Patent Application No. 16784357.2, Communication pursuant to Rules 161(1) and 162 EPC, dated Jun. 7, 2018, 3 pages.
U.S. Appl. No. 15/759,165 entitled "Gas Detector With Normalized Response and Improved Sensitivity", filed Mar. 9, 2018, 51 pages.
PCT Application No. PCT/US2016/020637, International Search Report, dated Jun. 15, 2016, 3 pages.
PCT Application No. PCT/US2016/020637, Written Opinion of the International Searching Authority, dated Jun. 15, 2016, 6 pages.
PCT Application No. PCT/US2016/020637, International Preliminary Report on Patentability, dated Sep. 5, 2017, 7 pages.
Europe Patent Application No. 16710887.7, Communication pursuant to Rules 161(1) and 162 EPC, dated Oct. 12, 2017, 2 pages.
Europe Patent Application No. 16766771.6, Communication Pursuant to Rules 161(1) and 162 EPC, dated Apr. 18, 2018, 3 pages.
Europe Patent Application No. 16766770.8, Communication pursuant to Rules 161(1) and 162 EPC, dated Apr. 17, 2018, 3 pages.
U.S. Appl. No. 15/759,165, Office Action dated Jan. 25, 2019, 15 pages.
U.S. Appl. No. 15/555,762, Office Action dated Dec. 31, 2018, 9 pages.
Europe Patent Application No. 16785292.0, Examination Report, dated Mar. 13, 2019, 12 pages.

ELECTROMAGNETIC RADIATION DETECTOR USING A PLANAR GOLAY CELL

CROSS-REFERENCE TO RELATED APPLICATIONS

The present application claims priority to and is the National Stage of International Application No. PCT/US2016/055759, filed Oct. 6, 2016 by Wei Yang, et al. and entitled "Electromagnetic Radiation Detector Using A Planar Golay Cell," which claims priority to U.S. Provisional Patent Application No. 62/239,685, filed Oct. 9, 2015 by Wei Yang, et al, and entitled "Electromagnetic Radiation Detector Using A Planar Golay Cell," both of which are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A Golay cell is a type of electromagnetic radiation detector that consists of an enclosure containing an optic absorbing material and a flexible diaphragm or membrane. It works by converting absorbed optic radiation into heat causing the absorbing material to expand, resulting in a pressure rise that can then be detected. The conversion from radiation to heat has been accomplished via a membrane absorber which, in general, is not wavelength specific.

When using a Golay cell as a detector in, for example, a non-dispersive infrared (NDIR) gas detection, it is valuable for the Golay cell to have high spectral correlation with the target gas. One approach is to fill the cell with IR absorbing gases that have the same or similar absorption spectrum as the target gases.

However, in comparison with a membrane absorber, a gas absorber has much less molecular density, thus a much thicker layer of gas is needed to achieve sufficient absorption. In addition, when the same level of absorption is achieved, the gas layer would possess a larger heat capacity than a solid membrane, thus lower temperature rise and sensitivity.

In many applications, it is also desirable for the detector to have a planar, or a small overall form factor, which is difficult to implement when the gas absorber demands a long optical path length. Alternatively, although a membrane absorber with an external filter would provide the spectral selectivity, it tends to be expensive and the filters are often sensitive to the angle of the incoming light.

SUMMARY

In an embodiment, an electromagnetic radiation detector device using a planar Golay cell may comprise a cell body forming a cavity therein, wherein the cavity includes a wavelength selective absorber having a predetermined absorption spectral range and the cavity is filled with a gas; and a pressure sensing element fluidly connected to the cavity to measure a change in pressure within the cavity.

In an embodiment, a method for using a Golay cell may comprise directing radiative power from a light source through at least a portion of a cell body of the detector toward the gas cavity and the wavelength selective absorber, wherein the optical path of the radiative power passes through one or more target gas before reaching the wavelength selective absorber; absorbing at least a portion of the radiative power by the wavelength selective absorber or the gas within the gas cavity; detecting, by a pressure sensing element, a pressure change caused by the absorbing of the radiative power; and determining an identity of the one or more target gas based on the detected pressure change.

In an embodiment, an electromagnetic radiation detector device using a planar Golay cell may comprise a cell body forming a cavity therein, wherein the cavity includes a wavelength selective absorber having a predetermined absorption spectral range and the cavity is filled with a gas having particular heat and thermal conductivity characteristics, and wherein at least a portion of the cell body is transmissive to at least the predetermined absorption spectral range; and a pressure sensing element fluidly connected to the cavity to measure a change in pressure within the cavity.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
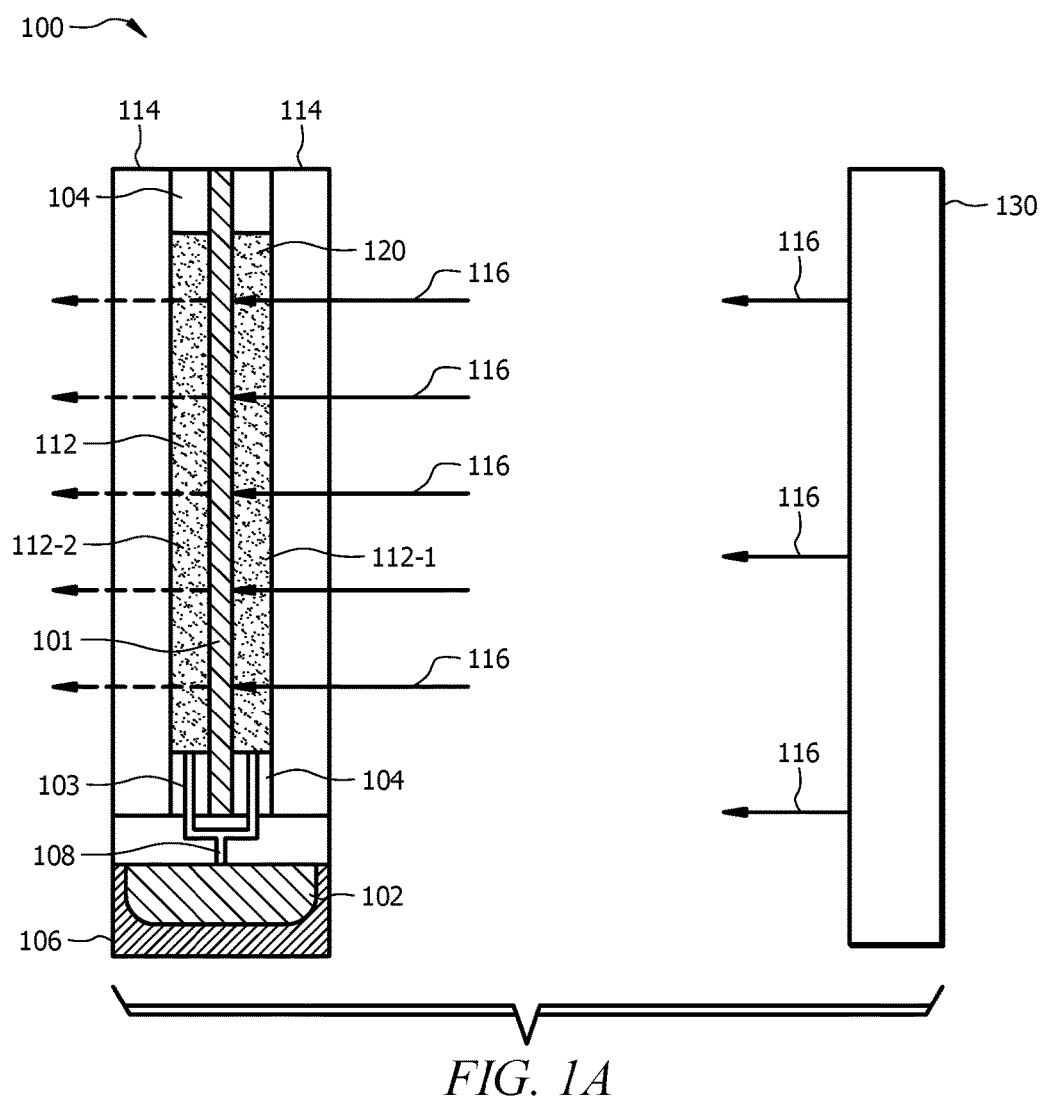
FIG. 1A illustrates an electromagnetic radiation detector device in accordance with one or more embodiments of the present disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include electromagnetic radiation devices, systems, and methods using a planar Golay cell. The present disclosure describes a spectrally selective membrane absorber which would enable the construction of a planar Golay cell of specific spectral characteristics and in extremely small form factors, in some embodiments.

One area in which the embodiments of the present disclosure can be beneficial is non-dispersive infrared (NDIR) gas detection, where the planar Golay cell can be used as a detector. Embodiments in such applications, offer the advantages of being planar, which can allow multiple cells to stack together, and can enable their use in compact designs. Additionally, the spectral selectivity allows embodiments that are specific to the intended analyte gases. This can allow for specialized applications and the ability to detect gases more accurately with, for example, reduced interferences from ambient gases, such as carbon dioxide ($CO_2$) or water.

One device includes a cell body forming a cavity therein. The cavity can include a wavelength selective absorber (or a film wavelength selective absorber) having a predetermined absorption spectral range, and the cavity can be filled with a gas having particular heat and thermal conductivity characteristics. The cell body can be transmissive to at least the predetermined absorption spectral range, and a pressure sensing element can be fluidly connected to the cavity to measure a change in pressure within the cavity.

As an example, planar Golay cells sensitive to wavelengths corresponding to the hydrocarbon absorption, in some embodiments, are illustrated in the attached drawing. The cells can have a suspended thin film polymer absorber, which can be conveniently made of, for example, foils of polyethylene, polypropylene, or other polymer material of specific, desired absorption spectra. The cell can be filled with a gas of low specific heat and low thermal conductivity, such as, for example, argon, krypton, or xenon.

In some embodiments, the total volume of the gas can be kept relatively small. For example, the spacing between the polymer membrane and the cell body can be between about 0.05 mm and about 0.2 mm.

The membrane thickness can be comparable or smaller than the light absorption length. For example, a suitable thickness may be between about 5 microns and about 15 microns. When the incident light is absorbed by the membrane, the membrane can be heated to a temperature above the ambient temperature. In this manner, the enclosed gas will be subsequently heated to nearly the same temperature of the membrane because the total gas heat capacity is much smaller than the membrane. The pressure rise of the heated gas can then be detected by the microphone which is fluidly connected to the cell. The resulting response as measured by the microphone can then be used to determine a concentration of a gas in the light path.

More specifically, the incident light can be modulated at a predetermined frequency to produce a resulting modulated pressure rise and fall within the cavity. The resulting pressure signal can then be detected at the predetermined modulation frequency, and the resulting magnitude of the modulated signal can be used to determine various properties of the light absorption between the light source and the cell. In general, a decreased signal would tend to indicate an increased concentration of a gas between the light source and the cell that absorbs in the specific wavelengths absorbed by the membrane, where the absorption in the gas reduces the amount of light reaching the membrane and therefore the output response.

Referring now to FIG. 1A, an electromagnetic radiation detector device 100 is shown. In the embodiment of FIG. 1A, the wavelength selective absorber 101 is maintained in position by spacers 104. On the end of the cell body 114, the spacers 104 also comprise at least one pressure sensing aperture 108 which is in fluid communication with a cavity 112 such that pressure sensing element 102 can sense changes in the pressure within the cavity 112 via the pressure sensing aperture 108.

In the embodiments of the present disclosure, at least a portion of the cell body 114 is transmissive to electromagnetic radiation. For example, the cell body 114 can be opaque to all light that is not within a particular range of wavelengths, such as those wavelengths that indicate the presence of a particular target gas. It should be noted that the embodiments of the present disclosure are not limited to gas detection and can be used to detect other items that can be identified using such devices.

Some embodiments can be used to identify particular gases, and therefore the electromagnetic radiation detector device 100 can be sensitive to a predetermined absorption spectral range that includes the spectral range of the gas or gasses being targeted for sensing. Accordingly, in some embodiments, at least portion of the cell body 114 can be transmissive to only that predetermined absorption spectral range or can be transmissive to at least that predetermined absorption spectral range.

In some embodiments, the cell body 114 can include optical characteristics that change the characteristics of the light passing through the cell body 114. For example, the cell body 114 can have a diffusing or collimating characteristic designed into the cell body 114. In some embodiments, the cell body 114 could also be a lens or waveguide.

These optical characteristics can be accomplished based on the formation of the interior of the cell body 114, the formation and/or preparation (e.g., polishing) of one or more sides of the cell body 114, and/or through the use of coatings applied to the cell body 114 on one or more sides. The cell body 114 can also be coated with optical films to enhance or retard the transmission of light at certain wavelengths. This may be beneficial in some embodiments to isolate or focus certain wavelengths for purposes of improving detection. For example, certain wavelengths that can be isolated or enhanced can be 3.3 and/or 3.4 microns for hydrocarbons, 4.3 microns for $CO_2$, or 9 microns for ammonia, among others.

In the embodiments of the present disclosure, the cavity 112 can be a closed cell that does not allow interaction with the ambient surroundings. Accordingly, the gas 120 within the cavity 112 can be selected to enhance the sensitivity for the presence of a particular gas or a particular set of gases.

In some embodiments, the cavity 112 is sealed such that ambient (or any other) gas cannot enter the cavity 112 once it is sealed. The cavity 112 can also be sealed such that gas cannot leak out of the cavity 112 once it is sealed. In some such embodiments, the pressure sensing element 102 and/or the cell body 114 can be attached such that the cavity 112 is hermetically sealed. Such embodiments allow for formation of a gas filled cavity 112 which is fluidly connected to the pressure sensing aperture 108 (e.g., microphone inlet port) but insulated from the ambient conditions.

In some embodiments, the gas 120 within the cavity 112 may be known, and the electromagnetic radiation detector device 100 may be configured to determine the characteristics and/or identity of a gas located within a separate gas chamber, wherein the light source 130 may be directed through the separate gas chamber. In some embodiments, the gas being measured may be present at any point between the light source 130 and the cavity 112, with or without being constrained to a particular chamber. In some embodiments, the gas being measured may be within the open/ambient air between the light source 130 and the cavity 112.

As shown in FIG. 1A, the cavity 112 of the planar Golay device may have two sides 112-1 and 112-2 that are separated by the wavelength selective absorber 101. In such embodiments, the electromagnetic radiation detector device 100 may be further provided with vias 103 to allow fluidic connection between the two sides 112-1 and 112-2 of the cavity 112 separated by the wavelength selective absorber 101.

In the embodiment of FIG. 1A, vias 103 can be formed in the cell body 114 (e.g., spacers 104) to allow fluid (e.g., gas 120 within the cavity 112) to move between the two sides 112-1 and 112-2 of the cavity 112. In this manner, pressure between the two sides 112-1 and 112-2 can be equalized, among other benefits. When radiative power 116 (e.g., light from a light source 130) enters the cavity 112 through the cell body 114 and is absorbed by the gas 120 and/or wavelength selective absorber 101 surfaces, a small amount of heat can be generated. The heat causes a pressure rise which can be sensed by the pressure sensing element 102.

The gas 120 in the cavity 112 can be selected to optimize the sensitivity and/or temperature range of the detector device 100, based on parameters such as specific heat, thermal conductivity, permeability, triple point, and/or chemical stability, among other parameters that can be utilized based upon the operating conditions of the electromagnetic radiation detector device 100. The gas 120 can, for example, be nitrogen, hydrogen, argon, krypton, xenon, hydrocarbons, fluorocarbons, or a mixture of above gases, among other suitable gas types. In various embodiments, the pressure of the gas 120 can be less or more than the ambient pressure. For example, the gas 120 pressure can range from 0.1 bar to 10 bar, in some embodiments.

An advantage of the electromagnetic radiation detector device 100 is the isolation of the microphone (or pressure sensing element) 102 from the ambient surroundings, thus eliminating interferences and instabilities due to environmental variables such as acoustic noise, pressure, density, moisture, chemicals, and particulates that are in the ambient surroundings around the electromagnetic radiation detector device 100. This may be accomplished by sealing the pressure sensing element 102 around the pressure sensing aperture 108. Also, this may be accomplished by a cap 106 located around the pressure sensing element 102.

Figure 1B:
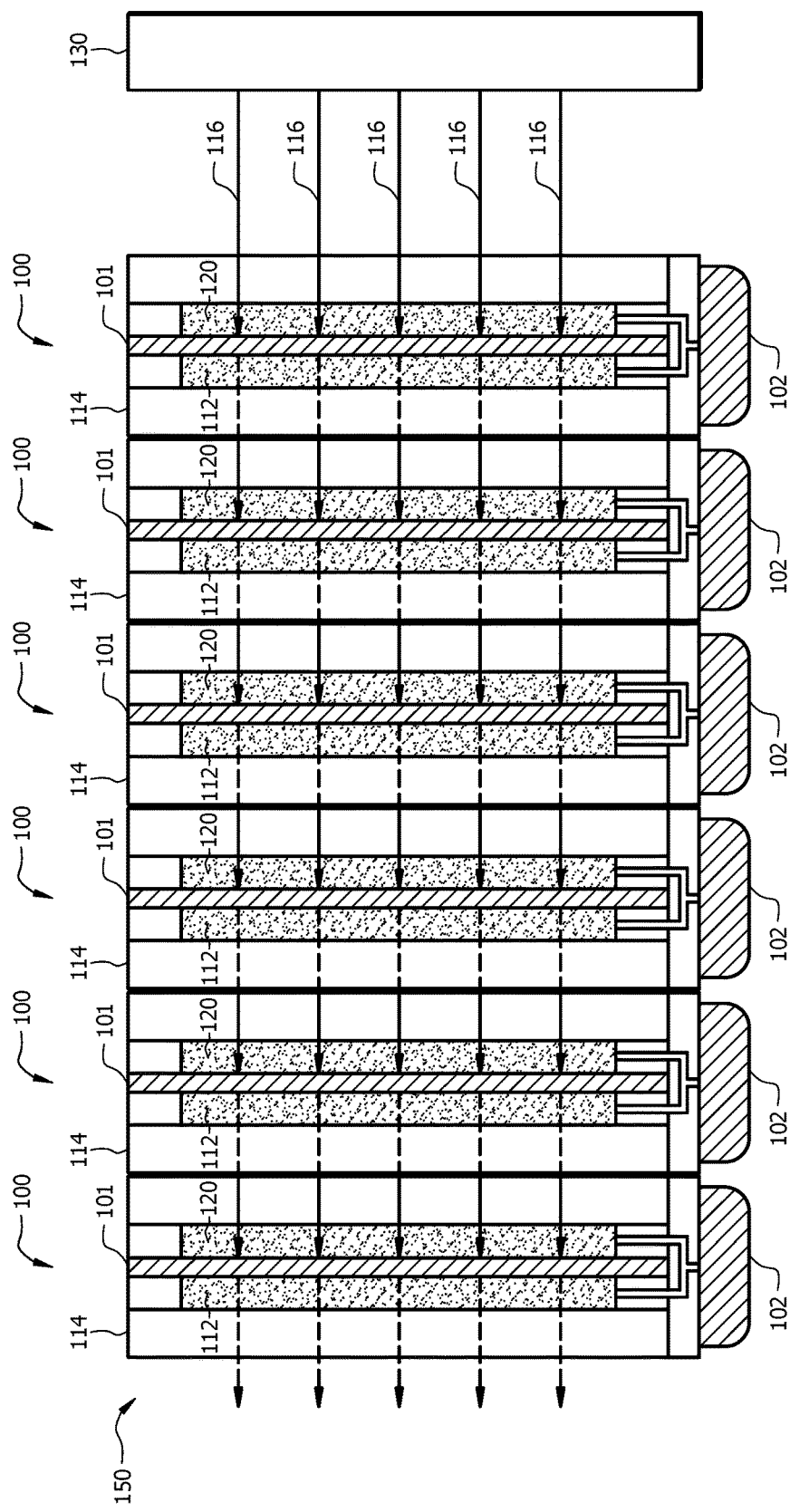
FIG. 1B illustrates a stacked electromagnetic radiation detector device in accordance with one or more embodiments of the present disclosure.

Referring now to FIG. 1B, in some applications, several of the electromagnetic radiation detector devices 100 (e.g., on the same substrate, such as a printed circuit board (PCB)) could be present, each having different gases 120 in their respective cavities 112, and they could be inserted into a larger system, to accomplish gas detection. Additionally, in some embodiments, a single electromagnetic radiation detector device 100 (e.g., the structure of FIG. 1A or a similar structure) could be used in a system and that electromagnetic radiation detector device 100 could be removed and replaced with another that could sense one or more other gases. In other embodiments, multiple electromagnetic radiation detector devices 100 could be used at the same time in a system 150 to sense multiple gases or could have the same gas 120 in the cavity 112 and could provide redundancy, which could be beneficial as it would provide increased certainty that the gas detection was correct. In some embodiments, a single light source 130 may be used to direct radiation or light through the plurality of electromagnetic radiation detector devices 100, wherein each cell body 114 may be transparent to a certain range of wavelengths. In some embodiments, the electromagnetic radiation detector devices 100 may be placed in a particular order such that the wavelengths that are filtered by the wavelength selective absorbers 101 may be absorbed in a particular order. Each of the electromagnetic radiation detector devices 100 may function as described in FIG. 1A.

Figure 2:
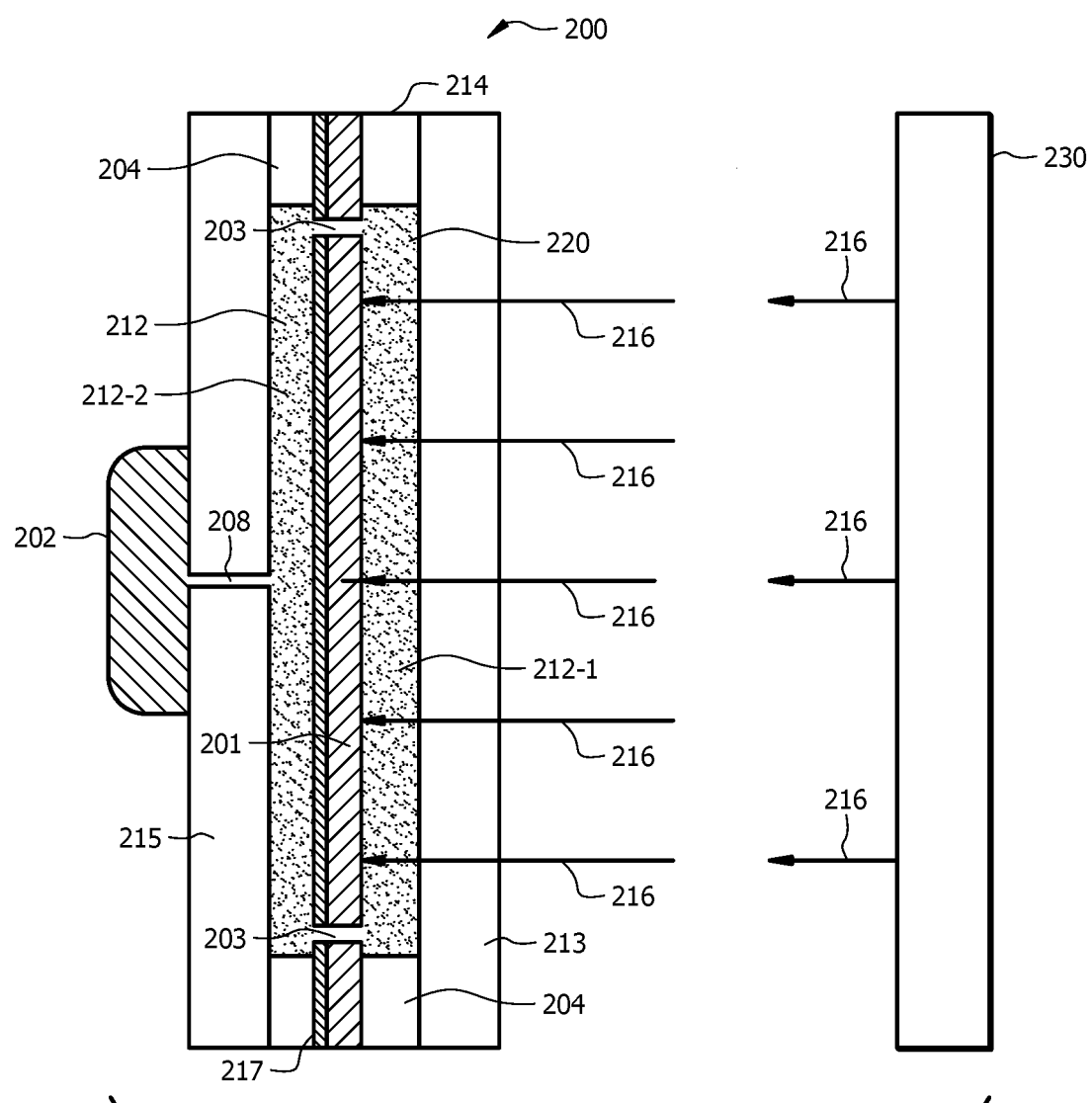
FIG. 2 illustrates another electromagnetic radiation detector device in accordance with one or more embodiments of the present disclosure.

FIG. 2 illustrates another electromagnetic radiation detector device 200 in accordance with one or more embodiments of the present disclosure. Similar to the embodiment of FIG. 1A, in the embodiment illustrated in FIG. 2, the electromagnetic radiation detector device 200 includes a cell body 214 having a cavity 212 formed therein, with a wavelength selective absorber 201 and a pressure sensing element 202 (e.g., a microphone) having a pressure sensing aperture 208 in fluid communication with the cavity 212.

In an embodiment, the cell body 214 has a front portion 213 and a back portion 215 wherein the pressure sensing element 202 is located on the back portion of the cell body 215 which also includes the pressure sensing aperture 208 which is in fluid communication with the cavity 212 such that pressure sensing element 202 can sense changes in the pressure within the cavity 212 via the pressure sensing aperture 208. Although not a requirement, the wavelength selective absorber 201 is also shown as being aligned along a center elongate axis of the cell body 214. In the embodiment of FIG. 2, the wavelength selective absorber 201 is also maintained in position by spacers 204.

In some embodiments, the gas 220 within the cavity 212 may be known, and the electromagnetic radiation detector device 200 may be configured to determine the characteristics and/or identity of a gas located within a separate gas chamber, wherein the light source 230 may be directed through the separate gas chamber. In some embodiments, the gas being measured may be present at any point between the light source 230 and the cavity 212, with or without being constrained to a particular chamber. In some embodiments, the gas being measured may be within the open/ambient air between the light source 230 and the cavity 212.

When radiative power 216 (e.g., light from a light source 230) enters the cavity 212 through the cell body 214 and is absorbed by the gas 220 and/or wavelength selective absorber 201 surfaces, a small amount of heat can be generated. As with the embodiment of FIG. 1A, the heat causes a pressure rise which can be sensed by the pressure sensing element 202 via the pressure sensing aperture 208. As discussed above with respect to FIG. 1A, the embodiment of FIG. 2 also includes one or more vias 203 to allow fluidic connection between two sides of the cavity 212-1 and 212-2 separated by the wavelength selective absorber 201. In the embodiment of FIG. 2, vias 203 can be formed in the wavelength selective absorber 201 (and a reflective element 217) to allow fluid (e.g., gas 220 within the cavity 212) to move between the two sides 212-1 and 212-2 of the cavity 212. In this manner, pressure between the two sides 212-1 and 212-2 can be equalized, among other benefits. In some embodiments, this functionality can be provided by other methods. For example, the wavelength selective absorber 201 can be gas-permeable or micro channels can be provided in the wavelength selective absorber 201 or in the cell body 214.

The embodiments disclosed herein can be coupled with a light source 230. For example, a suitable light source 230 can be one or more filament bulbs, microelectromechanical systems (MEMS) hotplates, light emitting diodes (LEDs), and/or lasers. Such components can all potentially be advantageously paired with detector embodiments described herein to provide a gas sensor with good performance.

In the embodiment of FIG. 2, a reflective element 217 is also provided located on the back side of the wavelength selective absorber 201. In some embodiments, the reflective element 217 can be near the back surface of the wavelength selective absorber 201, but does not need to be adjacent or connected thereto. Additionally, the reflective element 217 can be positioned on at least one side of the wavelength selective absorber 201. This can be beneficial, for example, as the reflection can be only a partial reflection of light impinging on the reflective element 217 and/or it could be applied to multiple sides of the wavelength selective absorber 201 to enhance some characteristics of the light within the cavity.

The reflective element 217 does not need to be reflective to visible light in all applications, but rather, may be reflective to one or more wavelengths that will be used with respect to detecting the particular one or more gases within the cavity 212. The reflective element 217 may be beneficial in, for example, reducing noise that may impinge on the pressure sensing aperture 208 via the front surface 213 of the cell body 214. In order to be sensitive to specific gases, optical band-pass filters may be added as additional components in the optical path or a coating on the interior surface (nearer to the pressure sensing element 202) or the exterior surface (or front surface 213) of the cell body 214. In some instances, even though the cavity 212 has a particular gas 220 therein, there may still be a need for filtering of ambient components that may have similar characteristics as the particular gas 220 in the cavity 212.

In such situations, one or more filters, such as thin film, applied coatings, filters physically separate from the cell body, or other types of filters, could be placed in the optical path of the radiative power 216 from the light source to filter out such ambient noise (characteristics that may be mistaken for the target gas in the optical path) associated with these ambient components. Such an implementation may also be done in applications having multiple gases 220 within the cavity 212. Examples of ambient components that can be filtered can, for example, include $CO_2$, water vapor, or condensed water, among others.

In an embodiment, the light source 230 can emit narrow or broadband electromagnetic radiation in the infrared region. In an embodiment, the light source 230 can include an incandescent lamp, a black-body radiation source, or another emitter of electromagnetic radiation in the infrared spectrum. In some embodiments, the light source 230 can be a light emitting diode (LED), an array of LEDs, a laser, a laser diode, or the like. In an embodiment, the light source 230 can produce a broadband radiation in the infrared range.

The radiation 216 from the light source 230 can be modulated to provide the acoustic response in the gas cavity 212. Various types of modulators can be used. In an embodiment, the light source 230 can be modulated and/or the radiation 216 can be mechanically or electrically modulated after being produced by the light source 230. For example, a controller can control the power signal to the light source 230 to produce a modulated radiation output. The radiation 216 can also be modulated after being produced by the light source 230, including the use of modulation mechanisms such as mechanical choppers (e.g., a rotating disc with passages therethrough, a rotating mirror, etc.), interference gratings or filters, interferometers, or the like. In some embodiments, optical modulators can also be used to modulate the radiation 216 from the light source 230 including, but not limited to, acousto-optic modulation, electro-optic modulation, magneto-optic modulation, and the like.

The radiation 216 can be modulated at a frequency that allows the acoustic signal to be detected, and the detection limits of the acoustic sensor along with any background noise can be taken into consideration when selecting the modulation rate. The radiation 216 can be modulated at a frequency of at least about 1 Hz, or at least about 10 Hz, though in some embodiments, the radiation 216 can be modulated at a lower frequency. In some embodiments, the radiation 103 may be modulated at higher frequencies in order to decrease the sensitivity of the photoacoustic sensor 100 to acoustical background noise. In an embodiment, the radiation 216 may be modulated at a frequency between 3 Hz and 10,000 Hz.

The electromagnetic radiation detector device 200 of this configuration can be operated at extremely low power because the planar Golay cell is able to detect a very low level of radiative power 216 thus the light source 230 can be energized at correspondingly low levels.

Embodiments of the present disclosure can be constructed as a micro-Golay detector device wherein the width of the widest side of the pressure sensing element (i.e. the greatest dimension of the pressure sensing element) may be approximately 2-5 mm With such embodiments, these devices could be used in small and/or portable applications and such devices may have low power consumption when compared to devices on the magnitude of 10-20 mm width dimension. Another benefit of a micro-Golay device is the reduced ability of contaminants to get into the device, as well as reduced ambient noise.

The embodiments of the present disclosure can be used in a broad range of optical based gas detection including detection of flammable gases, toxic gases, and other environmentally relevant gases such as $CO_2$ and refrigerants. For example, a planar Golay cell detector device can be used as a standalone detector for electromagnetic radiation from deep UV to terahertz frequencies, among other implementations.

Some embodiments of the disclosure may comprise methods for assembling and/or using an electromagnetic radiation detector device (as described above). These methods may comprise assembling the elements of the detector device as they are described in FIGS. 1A-2. Additionally, a gas may be allowed to enter the cavity of the device. Then, the cavity may be sealed such that gas may not enter or exit the cavity. A light source may be directed at the device, wherein the light source may pass through at least a portion of the cell body. The gas and/or the wavelength selective absorber may absorb at least a portion the radiation from the light source, and heat may be generated by the absorption. The generated heat may cause a pressure change, which may be detected by the pressure sensing element that is in fluid communication with the cavity of the device. The detected pressure change may be related to the amount of radiation that was absorbed by the gas, and the identity of the gas may be determined.

In another embodiment, the light source may be directed through another gas chamber that is separate from the cavity described above, wherein the target gas may be located in the gas chamber.

In a first embodiment, an electromagnetic radiation detector device using a planar Golay cell may comprise a cell body forming a cavity therein, wherein the cavity includes a wavelength selective absorber having a predetermined absorption spectral range and the cavity is filled with a gas; and a pressure sensing element fluidly connected to the cavity to measure a change in pressure within the cavity.

A second embodiment can include the device of the first embodiment, wherein the pressure sensing element is a microphone.

A third embodiment can include the device of the first or second embodiments, wherein the cell body is opaque to all light that is not within a particular range of wavelengths.

A fourth embodiment can include the device of any of the first to third embodiments, wherein the cavity is sealed such that ambient gas cannot enter the cavity once it is sealed.

A fifth embodiment can include the device of any of the first to fourth embodiments, wherein the cavity is filled with a gas having a low specific heat characteristic.

A sixth embodiment can include the device of any of the first to fifth embodiments, wherein the cavity is filled with a gas having a low thermal conductivity characteristic.

A seventh embodiment can include the device of any of the first to sixth embodiments, wherein the pressure sensing element and cell body are bound together and hermetically sealed from an ambient environment.

An eighth embodiment can include the sensor of any of the first to seventh embodiments, wherein the wavelength selective absorber is a polyethylene material.

A ninth embodiment can include the device of any of the first to eighth embodiments, wherein the wavelength selective absorber is a polypropylene material.

A tenth embodiment can include the device of any of the first to ninth embodiments, wherein the device further includes a reflective element on at least one side of the wavelength selective absorber.

An eleventh embodiment can include the device of any of the first to tenth embodiments, wherein the pressure sensing element is located on a back side of the cell body.

A twelfth embodiment can include the device of any of the first to eleventh embodiments, wherein the device includes an aperture through a back side of the cell body that provides fluid communication between the pressure sensing element and the cavity.

A thirteenth embodiment can include the device of any of the first to twelfth embodiments, wherein the cavity has two sides and wherein at least one of the wavelength selective absorber or cell body includes one or more vias to allow fluidic connection between two sides of the cavity.

A fourteenth embodiment can include the device of any of the first to thirteenth embodiments, wherein the wavelength selective absorber is taut and supported within the cell body.

A fifteenth embodiment can include the device of the any of the first to fourteenth embodiments, further comprising a plurality of planar Golay cells, wherein the cell bodies of the plurality of Golay cells are stacked against one another, wherein the pressure sensing elements of the Golay cells are located adjacent to the stacked sides of the cell bodies, and wherein radiation from a single light source is directed through the plurality of Golay cells.

In a sixteenth embodiment, a method for using a Golay cell may comprise directing radiative power from a light source through at least a portion of a cell body of the detector toward the gas cavity and the wavelength selective absorber, wherein the optical path of the radiative power passes through one or more target gas before reaching the wavelength selective absorber; absorbing at least a portion of the radiative power by the wavelength selective absorber or the gas within the gas cavity; detecting, by a pressure sensing element, a pressure change caused by the absorbing of the radiative power; and determining an identity of the one or more target gas based on the detected pressure change.

A seventeenth embodiment can include the method of the sixteenth embodiment, further comprising further comprising adding a wavelength selective absorber within a gas cavity of a detector; allowing one or more gasses to enter the gas cavity of the detector; and hermetically sealing the gas cavity and the pressure sensing element from an ambient environment.

An eighteenth embodiment can include the method of the seventeenth embodiment, further comprising assembling a reflective element on at least one surface of the wavelength selective absorber.

A nineteenth embodiment can include the method of any of the twelfth to eighteenth embodiments, further comprising assembling the pressure sensing element with a printed circuit board (PCB).

In a twentieth embodiment, an electromagnetic radiation detector device using a planar Golay cell may comprise a cell body forming a cavity therein, wherein the cavity includes a wavelength selective absorber having a predetermined absorption spectral range and the cavity is filled with a gas having particular heat and thermal conductivity characteristics, and wherein at least a portion of the cell body is transmissive to at least the predetermined absorption spectral range; and a pressure sensing element fluidly connected to the cavity to measure a change in pressure within the cavity.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An electromagnetic radiation detector device using a planar Golay cell, comprising:
   a cell body forming a cavity therein, wherein the cavity is filled with a gas;
   a wavelength selective absorber positioned within the cavity having a predetermined absorption spectral range, wherein the wavelength selective absorber is configured to absorb radiative power from a light source and to heat the gas within the cavity, causing a change in pressure within the cavity; and
   a pressure sensing element fluidly connected to the cavity to measure a change in pressure within the cavity;
   wherein the pressure sensing element is a microphone.

2. The device of claim 1, wherein the device is planar based on the spacing between the wavelength selective absorber and the cell body being less than approximately 0.2 millimeters.

3. The device of claim 1, wherein the cell body is opaque to all light that is not within a particular range of wavelengths.

4. The device of claim 1, wherein the cavity is filled with a gas having a low specific heat characteristic.

5. The device of claim 1, wherein the cavity is filled with a gas having a low thermal conductivity characteristic.

6. The device of claim 1, wherein the pressure sensing element and cell body are hermetically sealed together.

7. The device of claim 1, wherein the wavelength selective absorber is a polyethylene material.

8. The device of claim 1, wherein the wavelength selective absorber is a polypropylene material.

9. The device of claim 1, wherein the device further includes a reflective element on at least one side of the wavelength selective absorber.

10. The device of claim 1, wherein the cavity has two side-portions and wherein at least one of the wavelength selective absorber or cell body includes one or more vias to allow fluidic connection between the two side-portions of the cavity.

11. An electromagnetic radiation detector device using a planar Golay cell, comprising:
    a cell body forming a cavity therein, wherein the cavity is filled with a gas;
    a wavelength selective absorber positioned within the cavity having a predetermined absorption spectral range, wherein the wavelength selective absorber is configured to absorb radiative power from a light source and to heat the gas within the cavity, causing a change in pressure within the cavity; and
    a pressure sensing element fluidly connected to the cavity to measure a change in pressure within the cavity;
    the device further comprising: a plurality of electromagnetic radiation detector devices comprising a respective plurality of pressure sensing elements, wherein the cell bodies of the plurality of electromagnetic radiation detector devices are stacked against one another such that the radiative power passes through the electromagnetic radiation detector devices in a particular order, and wherein radiation from a single light source is directed through the plurality of electromagnetic radiation detector devices in succession.

12. The device of claim 11, wherein the respective plurality of pressure sensing elements of the plurality of electromagnetic radiation detector devices are located adjacent to stacked sides of the cell bodies.

13. The device of claim 11, wherein the plurality of electromagnetic radiation detector devices are placed in a particular order such that the wavelengths that are filtered by the wavelength selective absorbers may be absorbed in a particular order.

14. The device of claim 11, wherein each cell body is transparent to a certain range of wavelengths.

15. The device of claim 11, wherein each of the pressure sensing elements is a microphone.

16. The device of claim 11, wherein at least one of the wavelength selective absorber or the cell body includes one or more vias.

17. A method for using a Golay cell, the method comprising:
    directing radiative power from a light source through at least a portion of a cell body of the detector toward the gas cavity and the wavelength selective absorber, wherein the optical path of the radiative power passes through one or more target gas before reaching the wavelength selective absorber;

absorbing at least a portion of the radiative power by the wavelength selective absorber or the gas within the gas cavity;

detecting, by a pressure sensing element, a pressure change caused by the absorbing of the radiative power; and determining an identity of the one or more target gas based on the detected pressure change.

18. The method of claim 17, further comprising:

adding a wavelength selective absorber within a gas cavity of a detector;

allowing one or more gasses to enter the gas cavity of the detector; and hermetically sealing the gas cavity and the pressure sensing element from an ambient environment.

19. The method of claim 17, further comprising assembling a reflective element on at least one surface of the wavelength selective absorber.

20. The method of claim 17, further comprising assembling the pressure sensing element with a printed circuit board (PCB).

* * * * *